United States Patent
Netke et al.

(10) Patent No.: US 6,939,860 B2
(45) Date of Patent: Sep. 6, 2005

(54) COMPOSITION AND METHOD FOR TREATMENT OF NEOPLASTIC DISEASES ASSOCIATED WITH ELEVATED MATRIX METALLOPROTEINASE ACTIVITIES USING CATECHIN COMPOUNDS

(75) Inventors: Shriran Netke, 15A Shiraji Nagtur (IN); Vadim Ivanov, Castro Valley, CA (US); Wahid M. Roomi, Sunnyvale, CA (US); Aleksandra Niedzwiecki, San Jose, CA (US); Matthias Rath, Twenteport Oost 3, NL-7609 RG Almelo (NL)

(73) Assignee: Matthias Rath, Palo Alto, CA (US)

( * ) Notice: Subject to any disclaimer, the term of this patent is extended or adjusted under 35 U.S.C. 154(b) by 0 days.

(21) Appl. No.: 10/041,427

(22) Filed: Jan. 8, 2002

(65) Prior Publication Data

US 2003/0130201 A1 Jul. 10, 2003

(51) Int. Cl.$^7$ .................... A61K 38/05; A61K 31/7048; A61K 31/401
(52) U.S. Cl. .................... 514/27; 514/453; 514/456; 514/824; 514/400; 514/44; 514/474; 514/50; 514/18; 514/251; 514/423; 514/440; 514/458; 424/283; 424/729; 424/401; 536/23.4; 536/24.3; 536/23.1; 536/23.2; 536/23.5; 435/6; 435/69.1
(58) Field of Search .................... 514/27, 453, 456, 514/824, 400, 44, 474, 50, 18, 251, 423, 440, 458; 424/283, 729, 401; 536/23.4, 24.3, 23.1, 23.2, 23.5; 435/6, 69.1; 549/354, 400

(56) References Cited

U.S. PATENT DOCUMENTS 5,962,517 A * 10/1999 Murad .................... 514/474

FOREIGN PATENT DOCUMENTS

WO    WO 00/76492 A1    12/2000

OTHER PUBLICATIONS

Demeule et al.,"Matrix metalloproteinase inhibition by green tea catechins", Biochimica et Biophysica Acta, vol. 1478, pp. 51–60,2000.*

International Search Report for International Application No. PCT/EP02/01005.

Stoner, D. G. et al., "Polyphenols as Cancer Chemopreventive Agents", Journal of Cellular Biochemistry, vol. 22, pp. 169–180, (1995).

Demeule, M. et al., "Matrix Metalloproteinase inhibition by green tea catechins", Biochimica et Biophysica Acta, vol. 1478, pp. 51–60, (2000).

Zhao, J.F. et al., "Green Tea Protects Against Psoralen Plus Ultraviolet A–Induced Photochemical damage to Skin", The Journal of Investigative Dermatology, vol. 113, No. 6, pp. 1070–1075, (1999).

Horie, H. et al., "Simultaneous determination of qualitatively important components in green tea infusions using capillary electrophoresis", Journal of Chromatography A., vol. 758, pp. 332–335, (1997).

(Continued)

Primary Examiner—Elli Peselev
Assistant Examiner—Devesh Khare
(74) Attorney, Agent, or Firm—Kenyon & Kenyon

(57) ABSTRACT

The present invention relates to a composition comprising a catechin compound, ascorbic acid, proline and lysine. The present invention also relates to a method for treating neoplastic disease using a composition comprising a catechin compound, ascorbic acid, proline and lysine.

8 Claims, 9 Drawing Sheets

Inhibitory Effects of Various Concentrations of Epigallocatechin Gallate (EGCG) on Cell Proliferation of Human Breast Cancer Cells

OTHER PUBLICATIONS

Mukhtar, H. et al., "Tea polyphenois: prevention of cancer and optimizing health [1-3]", American Society for Clinical Nutrition, vol. 71, pp. 1698S–1702S, (2000).

Ahmad, N. et al., "Green Tea Constituent Epigallocatechin–3–Gallate and Induction of Apoptosis and Cell Cycle Arrest in Human Carcinoma Cells", Journal of the National Cancer Institute, vol. 89, No. 24, pp. 1881–1886, (1997).

Sadzuka, Y. et al., "Modulation of cancer chemotherapy by green tea" Clin Cancer Res, vol. 4, No. 1, (1998).

Cao, Y. et al., "Angiogenesis inhibited by drinking tea" Nature, vol. 398, p. 381 (1999).

Jankun, J. et al., "Why drinking green tea could prevent cancer" Nature vol. 387, p. 561, (1997).

Chen, L. et al., "Absorption, Distribution, and Elimination of Tea Polyphenols in Rats" The American Society for Pharmacology and Experimental Therapeutics, vol. 25, No. 9, pp. 1045–1049 (1997).

Yang, C.S. et al., "Blood and urine levels of tea catechins after ingestion of different amounts of green tea by human volunteers" Laboratory for Cancer Research, vol. 7, No. 4, (1998).

Bell, J. RC. et al., "(+)–Catechin in human plasma after ingestion of a single serving of reconstituted red wine [1, 2, 3]", American Journal of Clinical Nutrition, vol. 71, No. 1, pp. 103–108 (2000).

Sherry Chow, H–H. et al., "Phase 1 Pharmacokinetic Study of Tea Polyphenols following Single–dose Administration of Epigallocatechin Gallate and Polyphenon E[1]", Cancer Epidemiology, Biomarkers & Prevention, vol. 10, pp. 53–58, (2001).

* cited by examiner

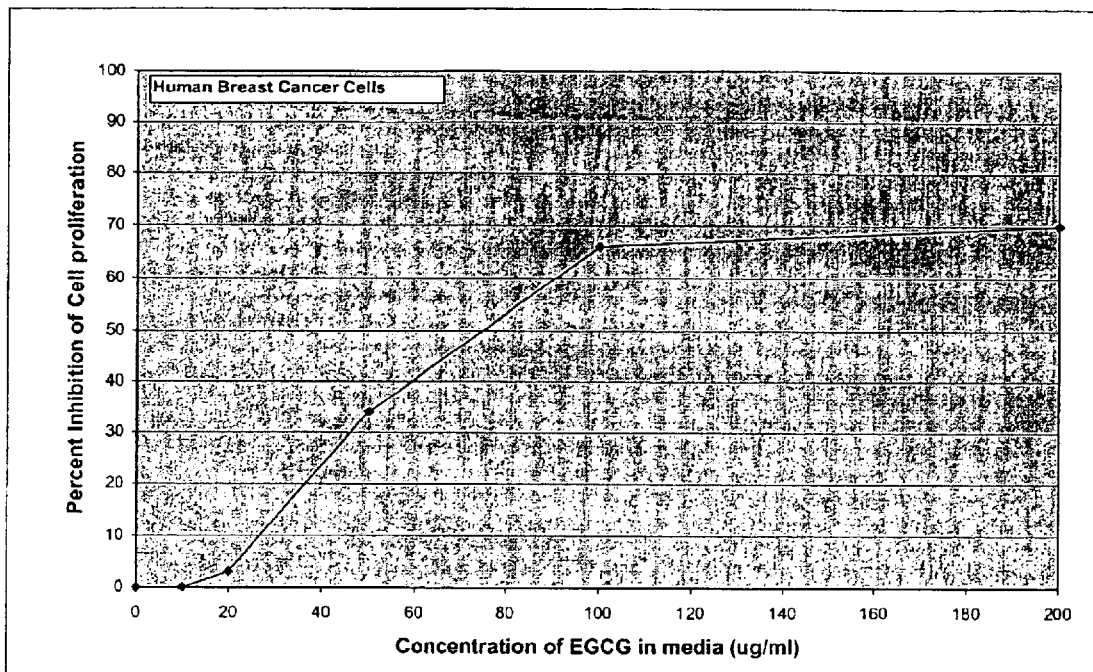
Figure 1: Inhibitory Effects of Various Concentrations of Epigallocatechin Gallate (EGCG) on Cell Proliferation of Human Breast Cancer Cells

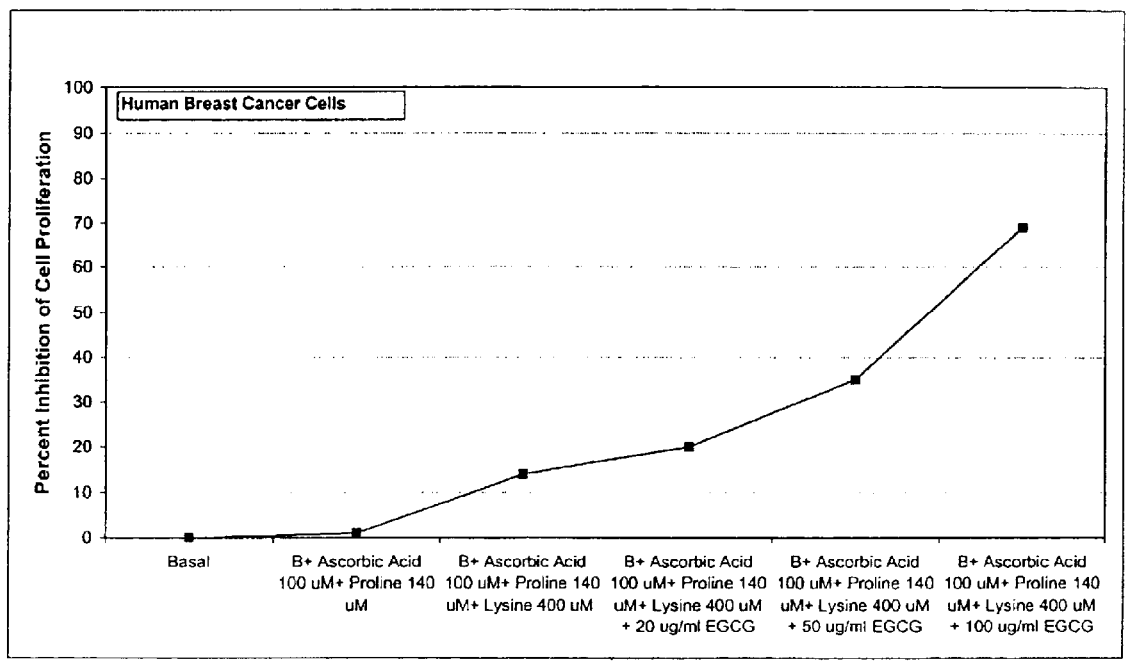
Figure 2 : Inhibitory Effects of Ascorbic Acid+Proline; Ascorbic Acid + Proline + Lysine; Ascorbic Acid + Proline + Lysine + Various Concentrations of Epigallocatechin Gallate (EGCG) on Cell Proliferation of Breast Cancer Cells

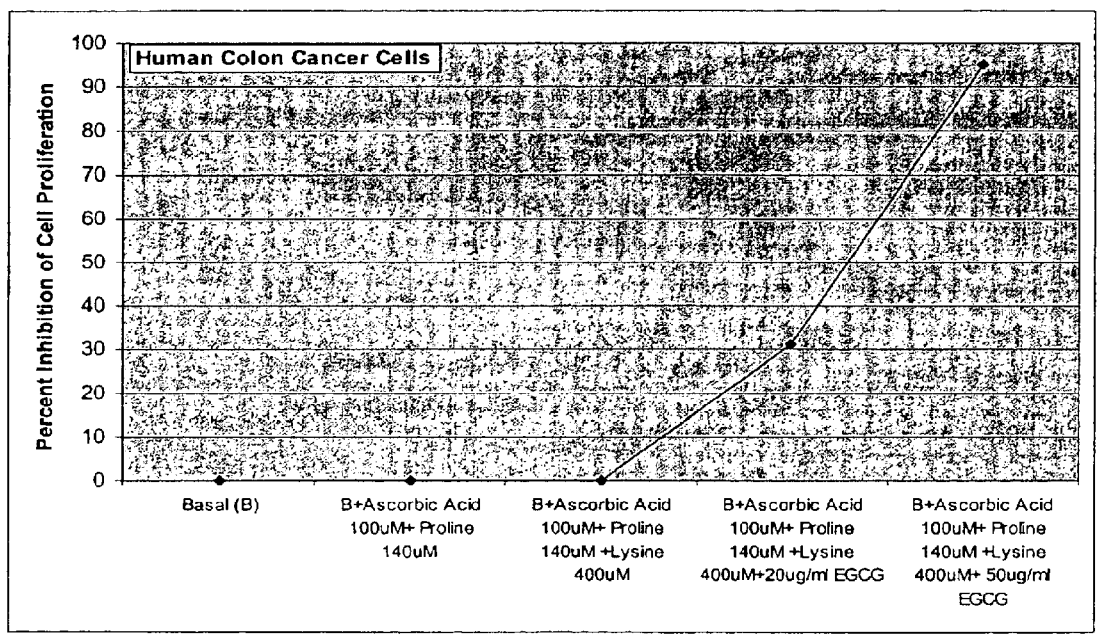
Figure 3 : Inhibitory Effects of Ascorbic Acid+Proline; Ascorbic Acid + Proline + Lysine; Ascorbic Acid + Proline+Lysine + Various Concentrations of Epigallocatechin Gallate (EGCG) on Cell Proliferation of Human Colon Cancer Cells

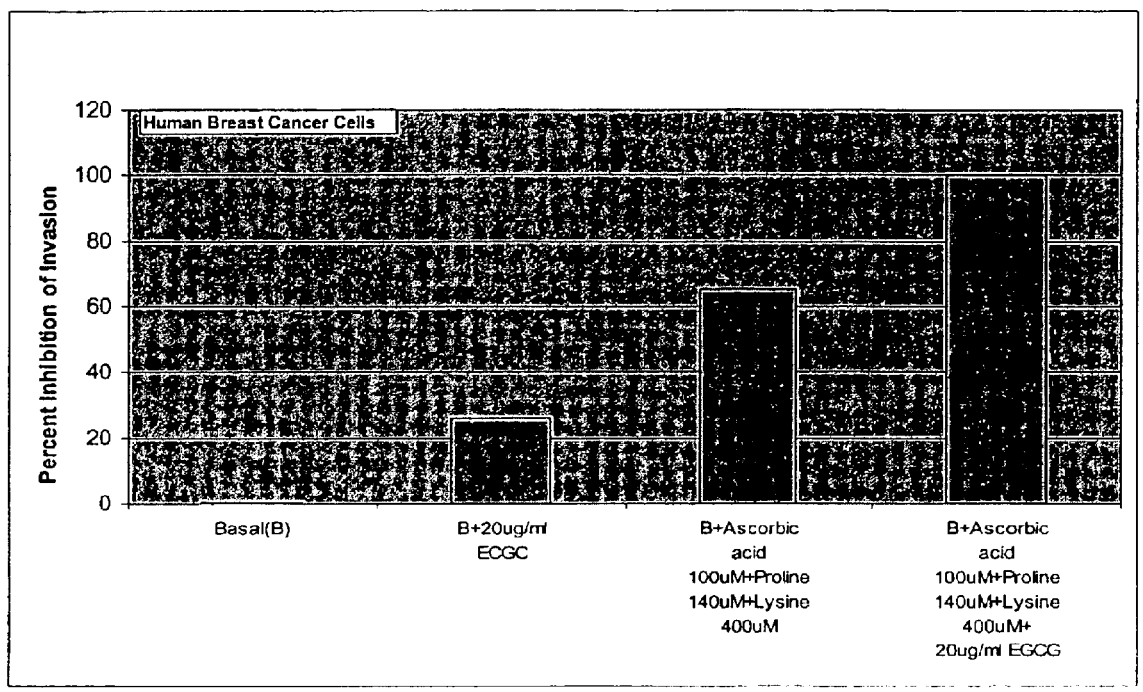
Figure 4 : Synergistic Inhibitory effect of Ascorbic Acid + Proline + Lysine and Epigallocatechin Gallate(EGCG) on Matrigel Invasion by Human Breast Cancer Cells

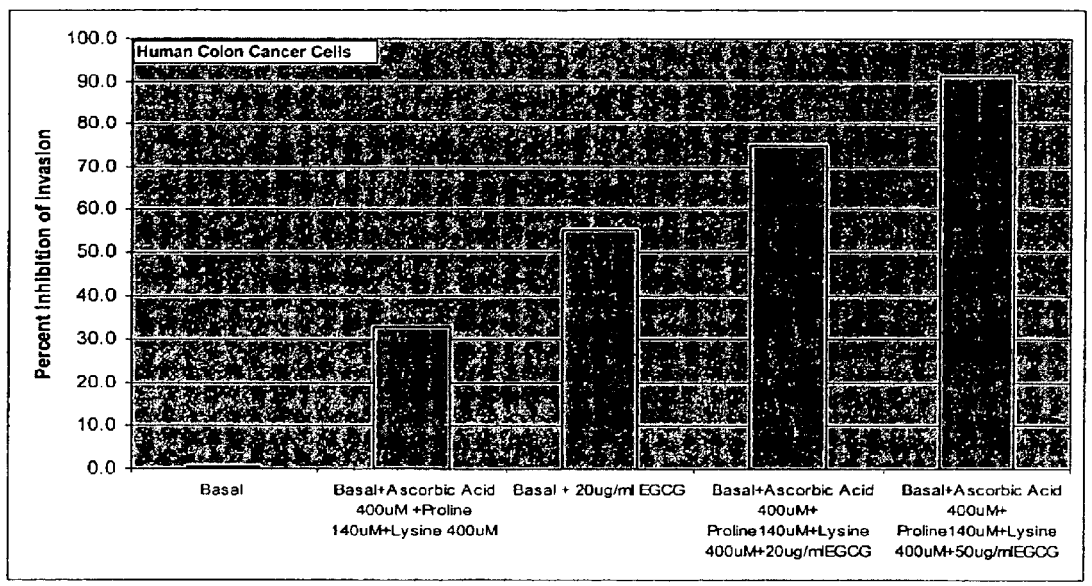
Figure 5 : Synergistic inhibitory effect of Ascorbic Acid + Proline + Lysine and Epigallocatechin Gallate(EGCG) on Matrigel Invasion by Human Colon Cancer Cells Lanes    1    2    3    4    5    6

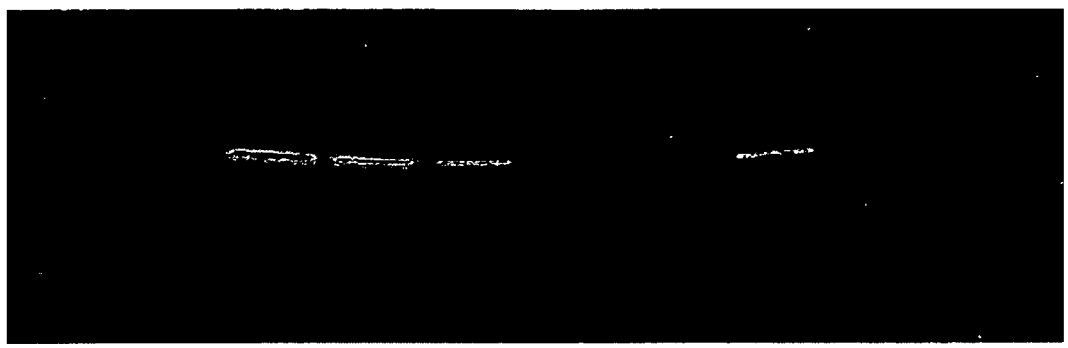

Figure 6: Inhibitory Effects of Ascorbic Acid 100uM +Proline 140uM + Lysine 400uM and Various Concentrations of Epigallocatechin Gallate (EGCG), on MMP2 production by Human Breast Cancer Cells.

Lane 1, Basal; Lane 2, Basal +Ascorbic Acid 100uM+ Proline 140uM + Lysine 400uM; Lane 3, Basal +Ascorbic Acid 100uM+ Proline 140uM + Lysine 400uM+ EGCG20ug/ml; Lane 4, Basal +Ascorbic Acid 100uM+ Proline 140uM + Lysine 400uM+ EGCG 50ug/ml; Lane 5, Basal +Ascorbic Acid 100uM+ Proline 140uM + Lysine 400uM+ EGCG 100ug/ml; Lane 6, Basal + 20ug/ml.

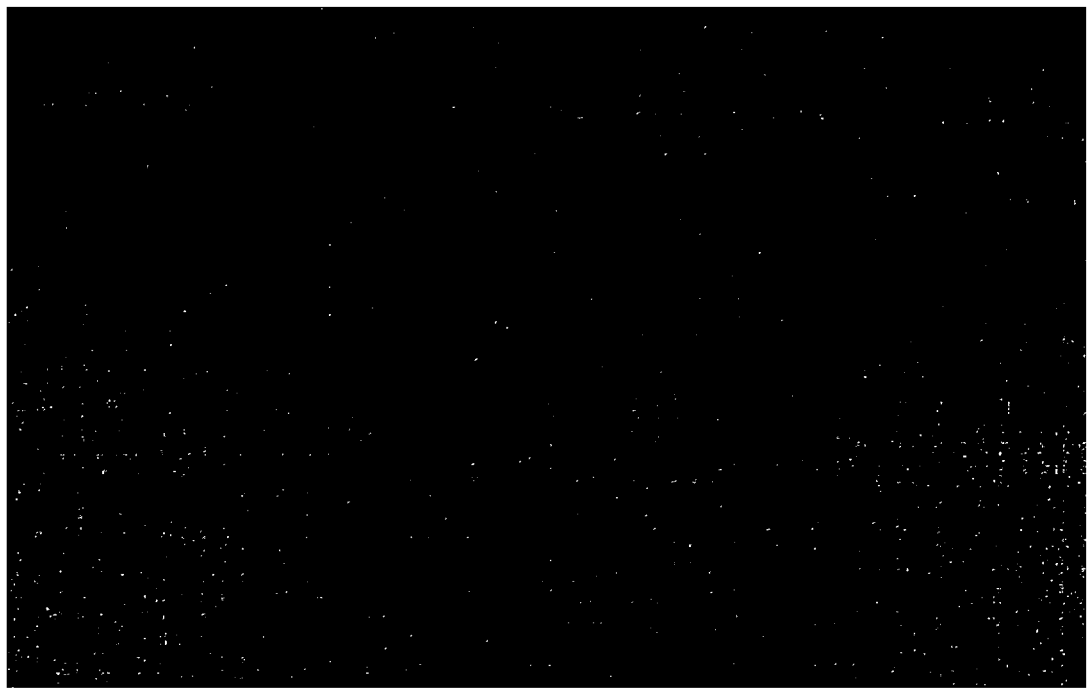
Figure 7: Normal Melanoma Cells

Figure 8: Apoptotic Effect of Addition of Ascorbic Acid 100uM, Proline 140uM, and Lysine 400uM, on Melanoma Cells. The cells are distended and nucleus is more deeply stained.

Figure 9: Apoptotic Effect of Addition of Ascorbic Acid 100uM, Proline 140uM, Lysine 400uM and EGCG 20ug/ml on Melanoma Cells. The cells are collapsed.

US 6,939,860 B2

COMPOSITION AND METHOD FOR TREATMENT OF NEOPLASTIC DISEASES ASSOCIATED WITH ELEVATED MATRIX METALLOPROTEINASE ACTIVITIES USING CATECHIN COMPOUNDS

FILED OF THE INVENTION

The present invention relates to the use of catechin compounds in combination with other dietary constituents in inhibiting matrix-metalloproteinases. More particularly, the present invention relates to the use of a composition comprising catechin, ascorbic acid, lysine and proline in treating neoplastic diseases.

BACKGROUND OF THE INVENTION

Polyphenolic compounds, also known as catechins, are present in green tea and have been suggested to provide protection against variety of illnesses including cancer (Mukhtar H., Ahmed N. Am. J. Clin. Nutr. 71: 1698S–1702S (2000)). Sadzuka et al. showed that oral administration of green tea enhanced the tumor-inhibitoy effects of doxorubicin in mice.

The anti-cancer activity of catechins may relate to their effects on several factors involved in proliferation of cancer cells and their metastasis. Catechins are known to cause cell cycle arrest in human carcinoma cells (Ahmad N., Feyes D. K., Nieminen A. L., Agarwal R., Mukhtar H. J. Natl. Cancer Inst. 89: 1881–1886 (1997)). Polyphenolic fraction from green tea is shown to protect against inflammation and cytokines induced by tumors.

Polyphenolic compounds present as 30% dry weight in green tea. They include flavanols, flavandiols, flavonoids, and phenolic acids. Flavanols are the most abundant among the polyphenols in green tea and are commonly known as catechins. There are four major catechins in green tea: 1) (–)-epicatechin, 2) (–)-epicatechin-3-gallate, 3) (–)-epigallocatechin, and 4) (–)-epigallocatechin-3-gallate (EGCG). Among the catechins, EGCG is the major polyphenolic constitutents present in green tea.

EGCG is a potent anti-oxidant compound (J. Cell. Biochem. 265: 236–257 (1996)) and may attribute to the anti-cancer activity of green tea. Catechin compounds were reported to exercise its anti-metastatic activity by preventing the angiogenesis process (Cao Y., Cao R. Nature 398: 381 (1999)). EGCG has also been shown to interfere with the activity of urokinase (u-plasminogen activator), one of the most frequently expressed enzymes in human cancers (Jankun J., Selman S. H., Swiercz R., Skrzypczak J. E. Nature: 387–567 (1997)).

However, it is established that the bioavailability of polyphenols in humans is extremely low (Chen L., Lee M. J., Yang C. S. Drug Metab. Dispos. 25: 1045–1050 (1997); Yang C. S., Chen L., Lee M. J., Balentine D. A., Kuo M. C., Schantz S. Cancer Epidemol. Biomark. Prev. 7: 351–35 (1998); Bell J. R., Donovan J. L., Wong R., Waterhouse H., German J. B., Walzem R. L., Kasim K. Am. J. Clin. Nutr. 71: 103–108 (2000); Sherry Chow H. H., Cai Y., Alberts D. S., Hakim I., Dorr R., Shahi F., Crowell J. A., Yang S. C., Hara H. Cancer Epidemol. Biomark. Prev. 10: 53–58 (2001)). The references cited are hereby incorporated by reference by its entireties. The low tissue concentration greatly reduces the therapeutic value of polyphenols including EGCG. There is a constant need in finding a better composition containing polyphenols that is effective in the treatment of neoplastic diseases. We surprisingly found a composition comprising catechins, ascorbic acid, proline, and lysine that can exert a potent anti-proliferative and anti-metastatic activity against neoplastic diseases.

SUMMARY OF THE INVENTION

The present invention relates to a composition of biochemical substances comprising a catechin, an anti-oxidant, proline and lysine that are effective in treating human diseases.

The present invention relates to a composition of biochemical substances comprising a catechin, an anti-oxidant, proline and lysine that are effective in inhibiting a matrix-metalloproteinase.

The present invention relates to a method of treating neoplastic diseases related to excessive degradation of extracellular matrix comprising administering an effective amount of a composition comprising a catechin compound, an anti-oxidant, proline and lysine.

BRIEF DESCRIPTION OF THE DRAWINGS

FIG. 1 depicts the inhibitory effects of EGCG on cell proliferation of breast cancer cells (MDA-MB 231).

FIG. 2 depicts the synergistic inhibitory effects of the combination of EGCG, ascorbic acid, proline, and lysine on cell proliferation of breast cancer cells (MDA-MB 231).

FIG. 3 depicts the synergistic inhibitory effects of the combination of EGCG, ascorbic acid, proline, and lysine on cell proliferation of colon cancer cells (HCT116).

FIG. 4 depicts that EGCG (20 $\mu$g/ml) inhibits the Matrigel invasion by breast cancer cells by about 25%. A combination of ascorbic acid, proline and lysine inhibits about 65%. A combination of ascorbic acid, proline and lysine with EGCG (20 $\mu$g/ml) completely inhibits (about 100%) the Matrigel invasion.

FIG. 5 depicts the combination of ascorbic acid, proline and lysine with the EGCG (20 $\mu$g/ml) synergistically inhibits to 100% of Matrigel invasion by melanoma cells (A2058).

FIG. 6 depicts a zymogram showing EGCG decreases the activity of MMP2 secreted by breast cancer cells.

FIG. 7 depicts the normal morphology of melanoma cells after the Matrigel invasion assay.

FIG. 8 depicts the changes induced by the combination of ascorbic acid, proline and lysine in the morphology of the melanoma cells.

FIG. 9 depicts the apoptotic effects of the combination of ascorbic acid, proline and lysine with EGCG.

DETAILED DESCRIPTION OF THE INVENTION

In another embodiment, the present invention relates to a composition comprising catechins present in tea extracts, red wine in combination with other dietary constituents, for synergistic effects, against neoplastic diseases and a variety of other illnesses. The dietary constituents covered by this application include, but are not limited to those detailed in this application.

Catechin compounds may be used in combination with other anti-oxidants such as vitamin E, glutathione, with other flavinoids, with facilitatory agents like folic acid and with metals like selenium which are known to suitably modify the activity of matrix-metalloproteinases, will enable us to reduce the effective concentration at which EGCG can manifest its anti-tumor activity.

In another embodiment, the present invention relates to a composition comprising catechins that is effective in reducing transformation of normal body cells into cancerous cells.

In another embodiment, the present invention relates to a composition comprising catechins that is effective in preventing cell proliferation of cancerous cells and in reducing synthesis, secretion and/or activity of various matrix-metalloproteinases that digest extra-cellular matrix (ECM).

In another embodiment, the present invention relates to a method of preventing and treating neoplastic conditions by administering such a composition comprising catechins, ascorbic acid, proline and lysine orally or by topical application.

The present invention is described in further detail with reference to the following examples, with no limitation of the invention implied.

General Experimental Conditions (a) Cell Lines

The following cancer cell lines obtained from ATCC were used in the studies:
  (i) Human Breast Cancer Cells MDA-MB 231
  (ii) Human Colon Cancer Cells HCT 116
  (iii) Human Melanoma Cells A 2058

(b) Cell Proliferation Studies

To study the effects of catechins and dietary composition on cell proliferation of human cancer cells, various human cancer cell lines were cultured in 24 well plates using the culture conditions specified by ATCC (supplier of cell lines). The cells were generally incubated for 3 to 4 days (before coalescence was reached). The total number of cells in a culture well was determined by staining the cells with vital stain (MTT) followed by the determination of OD of the stain solution. MTT only stain the dead cells and the amount of stain uptake correlates with the number of dead cells in the culture. Percent inhibition was calculated by comparing the OD of the treatment groups with the OD of the control groups.

(c) Matrigel Invasion Studies

The Matrigel Invasion studies were conducted using Matrigel (Becton Dickinson) inserts in compatible 24 well plates. This assay is a reliable assay for evaluating cancer metastasis.

Human fibroblast cells were seeded and grown in the 24-well plates using culture media containing ~10% serum. When the fibroblasts reached coalescence, the culture media with serum was withdrawn and replaced with fresh media without serum. A combination of catechin compounds plus dietary composition were added to the media without serum and human cancer cells were seeded on the upper surface of the Matrigel inserts.

After 18 hours, the media were withdrawn. Some media were saved for zymogram studies. The cells on the upper surface of the inserts were gently scrubbed away with cotton swab. The cells that had penetrated the Matrigel membrane and had migrated into the lower surface of the Matrigel were stained with Quick Stain and were counted under a microscope.

(d) Zymogram Studies

The media (25–30 $\mu$l) from Matrigel Invasion studies was applied to Novex zymogram gels (Invitrogen). The gel plates were developed and stained as recommended by the manufacturer. The matrix-metalloproteinases (MMPs) bands were identified on the basis of their known molecular weights.

(e) Morphological Studies

The morphology of human cancer cells that had migrated into the lower surface of the Matrigel membrane were stained with Quick Stain and were photographed under a microscope (100×).

EXAMPLE 1

Inhibitory Effects of Cpigallocatechin Gallate (EGCG) on Cell Proliferation of Human Breast Cancer Cells (MDA MB 231)

In these studies, $5 \times 10^4$ breast cancer cells (MDAMB 231) were seeded in each of the wells of 24-well plate. Control group refers to breast cancer cells that were grown in Liebovitz's media supplemented with 10% fetal bovine serum (FBS). Treatment group refers to breast cancer cells that were grown in Liebovitz's media supplemented with 10% fetal bovine serum (FBS) plus either 0, 10, 20, 50, 100 or 200 mg/ml of EGCG. Plates were incubated in ambient air (without supplemental $CO_2$) for a period of 4 days.

At the end of the period, the culture media were withdrawn and the cells in each well were stained with MTT. Excess MTT stain was washed off. The MTT stained cancer cells were dissolved in 1 ml DMSO solution. The optical density (OD) of the solution was determined for each well. The OD for the well was directly proportional to the number of dead cells. The OD of the MTT stained cancer cells that were previously cultured in the absence of EGCGT was used as a reference and was considered as 100. Percent inhibition was calculated by using the formula: % Inhibition=(OD of Reference−OD of the Test Treatment)/OD of Reference× 100%.

EGCG at 20, 50, 100 and 200 $\mu$g/ml caused 3, 34, 66 and 70% inhibition of cell proliferation of human cancer cells respectively (FIG. 1). EGCG at 10 ug/ml did not inhibit the cell proliferation.

EXAMPLE 2

Inhibitory Effect of A Combination of Ascorbic acid, Proline and Lysine with Various Concentrations of EGCG on Cell Proliferation of Human Breast Cancer Cells (MDA MB 231)

The general procedure of these studies remains to be the same as in Example 1.

In these studies, basal culture media were supplemented with the followings:
  i) ascorbic acid (100 uM)+proline (140 $\mu$M);
  ii) ascorbic acid (100 uM)+proline (140 $\mu$M)+Lysine (400 $\mu$M);
  iii) ascorbic acid (100 uM)+proline (140 $\mu$M)+Lysine (400 $\mu$M) plus 20 mg/ml EGCG;
  iv) ascorbic acid (100 uM)+proline (140 $\mu$M)+Lysine (400 $\mu$M) plus 50 mg/ml EGCG; or
  v) ascorbic acid (100 $\mu$M)+proline (140 $\mu$M)+Lysine (400 $\mu$M) plus 100 mg/ml EGCG Ascorbic acid+proline did not cause any inhibition of cell proliferation. Ascorbic acid+proline+lysine inhibited cell proliferation by about 14% (FIG. 2). A combination of ascorbic acid+proline+lysine plus 20 $\mu$g/ml of EGCG caused 20% inhibition (FIG. 2). 20 $\mu$g/ml of EGCG alone caused only 3% inhibition (Example 1). Thus, a combination of ascorbic acid, proline and lysine act synergistically with EGCG to inhibit cancer cell proliferation.

EXAMPLE 3

Inhibitory Effects of a Combination of Ascorbic acid, Proline and Lysine with Various Levels of EGCG on Cell Proliferation of Human Colon Cancer Cells (HCT116)

In this study, human colon cancer cells were grown in McCoy's 5A medium with 10% fetal bovine serum in 5%

$CO_2$ atmosphere. The general procedure and the treatment investigated were the same as used in Example 2.

A combination of ascorbic acid, proline and lysine with EGCG synergistically increased the inhibitory effects on cell proliferation from 0% to 31% at 20 ug/ml EGCG and to about 95% at 50 µg/ml EGCG (FIG. 3).

Inhibitory Effects of EGCG and a Combination of Ascorbic Acid, Proline and Lysine on Invasion of Matrigel by Cancer Cells

EXAMPLE 4

Inhibitory Effects of Graded Levels of EGCG and Combination of Ascorbic Acid, Proline and Lysine with Various Levels of EGCG on Invasion Through Matrigel by Breast Cancer Cells (MDA MB 231)

The general procedure for Matrigel Invasion Assay has been described above. In this assay, human breast cancer cells ($5 \times 10^4$) were seeded on each insert. Various supplements were added to Leibovitz's media. The plates were incubated in an incubator in ambient air without supplemental $CO_2$.

A composition comprising 20 or 50 µg/ml EGCG in the media inhibited the invasion by the breast cancer cells by about 26% and 100% respectively. While ascorbic acid (100 µM)+proline (140 µM)+lysine (400 µM) in the media caused 65% inhibition, a combination of ascorbic acid (100 µM)+proline (140 µM)+lysine (400 µM) plus 20 µg/ml of EGCG completely inhibited (100% inhibition) of cancer cell invasion (FIG. 4).

EXAMPLE 5

Inhibitory Effects of Graded Levels of EGCG and Combination of Ascorbic Acid, Proline and Lysine with Various Levels of EGCG on Invasion Through Matrigel by Human Melanoma Cells (A2058)

The general procedure for Matrigel Invasion assay has been described above. Human melanoma cells (A2058) ($5 \times 10^4$)were seeded on each insert. Various supplements were added to DMEM. The plates were incubated in an incubator under 5% $CO_2$ atmosphere.

While a combination of ascorbic acid (100 µM)+proline (140 µM)+lysine (400 µM) caused only 13% inhibition, a combination of ascorbic acid (100 µM)+proline (140 µM)+lysine (400 µM) plus 20 µg/ml EGCG completely prevented the invasion of melanoma cells through the Matrigel (FIG. 5).

Zymogram Studies

EXAMPLE 6

Effects of Graded Levels of EGCG on MMP2 Production by Human Breast Cancer Cells (MDA MB 231)

The media from various treatments in the Matrigel Invasion assay (Example 4) were applied to Novex Zymogram Gel (Invitrogen). The plates were developed and stained as recommended by the manufacturer. The matrix metalloproteinases (MMPs) bands were identified on the basis of their known molecular weights (FIG. 6).

Zymogram of the culture media from the Matrigel Invasion Assays indicated that 20 ug/ml EGCG in the media reduced the production of MMP2 and completely inhibited the production of MMP9 (FIG. 6). At concentrations of 50 µg/ml and 100 ug/ml of EGCG, the activities of both MMP2 and MMP9 were completely inhibited (FIG. 6).

Cell Morphology

EXAMPLE 7

Effects of EGCG and a Combination of Ascorbic Acid, Proline and Lysine on the Cell Morphology of Human Melanoma Cells (A2058)

The micrographs of the cancer cells in basal media as they migrated through the Matrigel are shown FIG. 7. Inclusion of the combination of ascorbic acid (100 µM)+proline (140 µM)+lysine (400 µM) in the media altered the morphology of the cells (FIG. 8). The distension of the cells with distinct enlargement of nucleus was evident. Addition of 20 ug/ml of EGCG to the combination of ascorbic acid (100 µM)+proline (140 µM)+lysine (400 µM) in the media caused extensive apoptotic changes (FIG. 9).

These findings described in the examples 1–7 indicate that a strong synergistic effect exerted by EGCG, when EGCG was used with a combination of ascorbic acid+proline+lysine. Therefore, these studies show a surprising synergistic effect of a combination of EGCG and ascorbic acid+proline+lysine makes it possible to take full advantage of anti-proliferative and anti-metastasis activity of EGCG at a comparatively low level of its tissue concentration.

Hence, the present findings are of immense importance as they can bring effective level of catechins closer to those, which can be achieved, in the tissues.

It has been suggested that the proliferation of cancer cells and up-regulation of their enzymes are caused by increased concentration of reactive oxygen species (ROS). In this situation, use of combinations of various biological antioxidants such as tocopherols, carotinoids, along with other facilitating agents like ubiquinols, biflavonoides, lipoic acid, carnitine will provide a more potent synergistic mixture for treatment of the above-mentioned maladies.

The present invention provides a surprising observation that a combination comprising catechin compounds would exert synergistic activity and thereby make it possible to achieve very efficient anti-cancer activity at lower levels of tissue catechins. The above findings open the possibility of using various constituents in combination of different constituents at effective levels for the prevention and treatment of neoplastic diseases.

One skill in the art will appreciate that proline and lysine are not merely limited to proline and lysine. The scope of the present invention is intended to cover lysine derivatives and its precursors, proline derivatives and its precursors.

One skill in the art will appreciate that the anti-oxidant, ascorbic acid, should cover the derivatives and precursors of ascorbic acid.

Other biological anti-oxidants include tocopherols and related compounds, trans-retinoic acid and related compounds, carotinoids and related compounds, glutathione and related compounds, ubiquinols and related compounds, folates and related compounds, bioflavonoids and related compounds as well as compounds of selenium.

Clinical Applications

The invention focuses on the preventive and therapeutic use of a catechin in combination with an anti-oxidant, proline and lysine. The combined use of a catechin with an anti-oxidant, proline and lysine increases the efficiency of the catechin compound in treating human diseases.

Human diseases include but are not limited to neoplastic diseases, inflammatory conditions, infectious diseases, cardiovascular diseases and other pathological conditions involving degradation of extra-cellular matrix. Such conditions include abnormal angiogenesis, pathological intravasation, rheumatoid and osteoarthritis, atherosclerosis, dilated cardiomyopathy, emphysema and other chronic conditions.

The present invention provides a method of treating and preventing human diseases involving degradation of extra-cellular matrix such as: i) neoplastic diseases; ii) inflammatory conditions (including but not limited to allergies, emphysema, rheumatoid arthritis, osteoarthritis, periodontitis, neurodermatitis); iii) infectious diseases (including but not limited to viral infections such as common cold, influenza, hepatitis, herpes, HIV; bacterial infections such as pneumonia, tuberculosis, meningitis, gonorrhea, syphilis, and or fungal diseases; iv) cardiovascular diseases (including but not limited to atherosclerosis, cardiomyopathy, restonosis after angioplasty); v) degenerative diseases (including but not limited to osteoporosis and arthritis); vi) neurological disorders (including but not limited to Alzheimer Disease, multiple sclerosis); and vii) autoimmune diseases (including but not limited to arthritis) by administering effective amounts of compositions described in this application.

What is claimed is:

1. A pharmaceutical composition of biochemical substances for use in treating a neoplastic disease in a human, comprising:

an anti-neoplastic disease therapeutically effective amount of a catechin compound selected from the group consisting of epicatechins, epigallocatechin, epicatechin gallate, and epigallocatechin gallate;

an anti-oxidant;

a proline; and a lysine, wherein the anti-oxidant, proline and lysine are in amounts sufficient to produce a synergistic effect in combination with the catechin compound that is therapeutically effective in inhibiting the activity of a matrix-metalloproteinase.

2. The composition according to claim 1, wherein the catechin compound is epigallocatechin gallate.

3. The composition according to claim 1, wherein the anti-oxidant is selected from the group consisting of ascorbic acid, tocopherols, tocotrienols, carotinoids, glutathione, alpha-lipoic acid, ubiquinols, bioflavonoids, and carnitine.

4. The composition according to claim 1, wherein the anti-oxidant is ascorbic acid.

5. The composition according to claim 1, wherein the anti-oxidant further comprises a folic acid.

6. The composition according to claim 5, wherein the folic acid is folate.

7. The composition according to claim 1, wherein the composition further comprises selenium in an amount sufficient to produce a synergistic effect in combination with the composition of claim 1.

8. The composition according to claim 7, wherein the selenium is selected from the group consisting of selinite and methyl selinate.

* * * * *